United States Patent
Fu et al.

(10) Patent No.: US 9,458,890 B1
(45) Date of Patent: Oct. 4, 2016

(54) SQUARE QUICK CONNECT INTERFACE

(71) Applicant: Holmed, LLC, Franklin, MA (US)

(72) Inventors: Rick Fu, Quincy, MA (US); Scott Foret, Allston, MA (US); Arnold Feinberg, Stoughton, MA (US); Frank Slauenwhite, III, Woburn, MA (US)

(73) Assignee: HOLMED, LLC, Franklin, MA (US)

( * ) Notice: Subject to any disclaimer, the term of this patent is extended or adjusted under 35 U.S.C. 154(b) by 428 days.

(21) Appl. No.: 13/722,555

(22) Filed: Dec. 20, 2012

(51) Int. Cl.
*F16D 1/04* (2006.01)
*B25B 23/00* (2006.01)

(52) U.S. Cl.
CPC ............ *F16D 1/04* (2013.01); *B25B 23/0035* (2013.01); *Y10T 403/592* (2015.01)

(58) Field of Classification Search
CPC . F16D 1/04; B25B 23/0035; B23B 21/1071; B23B 21/1072; B25G 3/18; B25G 3/26; Y10T 403/592; Y10T 279/17196; Y10T 279/17145; Y10T 279/17752
USPC ............ 403/321, 322.1, 322.2, 325; 279/75, 279/137, 904, 905; 81/177.85
See application file for complete search history.

(56) References Cited

U.S. PATENT DOCUMENTS

| | | | | |
|---|---|---|---|---|
| 4,621,821 A | * | 11/1986 | Schneider | B23H 7/26 219/69.11 |
| 4,692,073 A | | 9/1987 | Martindell | |
| 4,786,062 A | * | 11/1988 | Schneider | B23H 7/26 269/277 |
| 5,366,313 A | * | 11/1994 | LaBarre | 403/108 |
| 5,398,946 A | * | 3/1995 | Quiring | 279/30 |
| 5,951,024 A | * | 9/1999 | Montjoy et al. | 279/43 |
| 6,457,916 B2 | | 10/2002 | Wienhold | |
| 6,619,897 B2 | * | 9/2003 | Erickson et al. | 409/234 |
| 7,175,185 B2 | | 2/2007 | Chen | |
| 7,448,302 B2 | | 11/2008 | Huang | |
| 7,469,909 B2 | | 12/2008 | Strauch et al. | |
| 7,565,854 B2 | | 7/2009 | Chiang et al. | |
| 7,581,470 B1 | | 9/2009 | Huang | |
| 7,654,027 B1 | * | 2/2010 | Grover | 42/85 |
| 7,654,779 B2 | * | 2/2010 | Sasaki et al. | 408/240 |
| 7,669,860 B2 | | 3/2010 | Chiang | |
| 7,740,249 B1 | | 6/2010 | Gao | |
| 7,922,180 B2 | | 4/2011 | Meng | |
| 8,146,461 B1 | * | 4/2012 | Su | 81/177.85 |
| 2002/0071719 A1 | * | 6/2002 | Moore | 403/322.2 |
| 2003/0077136 A1 | * | 4/2003 | Rohm | 408/239 R |

(Continued)

OTHER PUBLICATIONS

U.S. Appl. No. Not Yet Assigned, filed Dec. 20, 2012 by Rick Fu et al. for a Improved AO Quick Connect Interface, pp. 1-22.

*Primary Examiner* — Jonathan Masinick
(74) *Attorney, Agent, or Firm* — Cesari and McKenna, LLP; James A. Blanchette

(57) ABSTRACT

In one embodiment, a quick connect interface for a surgical instrument includes a body having an outer surface and an inner surface that defines an inner cavity. One or more ball bearings are disposed in respective holes in the body. A locking pin is disposed on a ramp formed in the body. A sleeve surrounds a portion of the body and is slideable along the body, from an unlocked position to a locked position. The sleeve includes a camming ramp that urges the one or more ball bearings to partially extend through the holes into the inner cavity. One or more springs are arranged to urge the locking pin down the ramp, so that the locking pin partially extends through an opening into the inner cavity. The one or more ball bearings and the locking pin are positioned to urge the shaft to one side of the inner cavity.

26 Claims, 8 Drawing Sheets

(56) References Cited

U.S. PATENT DOCUMENTS

| | | |
|---|---|---|
| 2005/0036844 A1 | 2/2005 | Hirt et al. |
| 2005/0176283 A1 | 8/2005 | Cantlon |
| 2008/0087143 A1* | 4/2008 | Hsieh ......................... 81/177.85 |
| 2009/0026718 A1* | 1/2009 | Krondorfer ..................... 279/30 |
| 2009/0226248 A1* | 9/2009 | Wang ......................... 403/322.2 |
| 2009/0309316 A1* | 12/2009 | Hu ................................. 279/75 |

\* cited by examiner

SQUARE QUICK CONNECT INTERFACE

BACKGROUND

1. Technical Field

The present disclosure relates generally to surgical instruments, and more specifically to quick connect interfaces used to connect a shaft of a replaceable tool to a drive mechanism.

2. Background Information

Quick connect interfaces (or simply "quick connects") are widely used in surgical instruments to connect a shaft of a replaceable tool, such as a bit, to a drive mechanism, such as a ratcheting or non-ratcheting handle or a motor-operated drive. These surgical instruments may be used to perform a variety of surgical tasks, including drilling, reaming, tapping, placement of bone screws, assembly of spinal constructs, and the like. One common type of quick connect interface that may be employed is square quick connect interface, often a ¼ inch square (or simply "quarter square") quick connect interface. Such an interface may be used with a wide variety of different types of replaceable tools, as well as different drive mechanisms.

In a typical ¼ inch square quick connect interface, two ball bearings are generally, positioned radially about a central axis of the quick connect interface, about 180 degrees apart. The shaft may be retained in the interface by operation of these ball bearings, which engage a groove formed in the end of the shaft. The ball bearings are often held by a substantially straight walled portion of the sleeve.

However, while such an arrangement may prevent removal of a replaceable tool, it may not hold the tool very securely. There is often substantial axial and lateral play. There may be minor variations in the shaft of replaceable tools, such that diameters of the groove may vary from one replaceable tool to the next. However, ball bearings positioned radially about 180 degrees apart, and held by straight walled portions, cannot effectively adapt to such variation. This may results in each replaceable tool fitting differently. In some cases, the fit may result in excessive amounts of play, such that the surgical instrument has a generally "sloppy" feel. This feel may be unsettling to a surgeon trying to perform a delicate surgical procedure.

While certain attempts have been made to reduce lateral and axial play, these attempts have often compromised other aspects of the quick connect interface, rendering them impractical. For example, certain attempts have increased the size of the quick connect interface, for example, doubling its size. The increased size may impact the operation and feel of a surgical instrument.

Accordingly, there is a need for an improved quick connect interface.

SUMMARY

In one embodiment, an improved quick connect interface (e.g., an improved ¼ inch square quick connect interface) includes first and second ball bearings positioned in holes in a body, at locations substantially 90 degrees apart radially about a central axis, and includes a generally-cylindrical locking pin, positioned between the first and second ball bearings. A spring-loaded sliding sleeve may surround a portion of the body and slide from an unlocked position to a locked position. As the sleeve is slide from the unlocked position to the locked position, the ball bearings are urged by a camming ramp formed in the sleeve into the holes, so that they partially extend through the holes into an inner cavity of the body. When so urged, they may engage a groove formed in the shaft of a replaceable tool disposed therein.

Further, the locking pin may be guided by a shuttle. The shuttle may be disposed between first and second compression springs (e.g., identical wave springs). The compression springs may be arranged such that, when the sleeve is slide from the unlocked position to the locked position, one of the compression springs has a higher preload than the other. The compression spring with higher preload applies pressure upon the shuttle, which in turn urges the locking pin down the ramp so that it partially extends through an opening at the bottom of the ramp, into the inner cavity of the body. When so urged, the locking pin engages a portion of the shaft of the replaceable tool disposed therein (e.g., a corner of a substantially square part of the shaft).

The contact of the locking pin, along with the pressure applied by the ball bearings, may urge the shaft of the replaceable tool towards one side of the inner cavity of the body. Such urging may ensure contact despite variations in the shafts of replaceable tools, and reduce both lateral and axial play.

BRIEF DESCRIPTION OF THE DRAWINGS

The detailed description below refers to the accompanying drawings of example embodiments.

DETAILED DESCRIPTION OF EXAMPLE EMBODIMENTS

Figure 1:
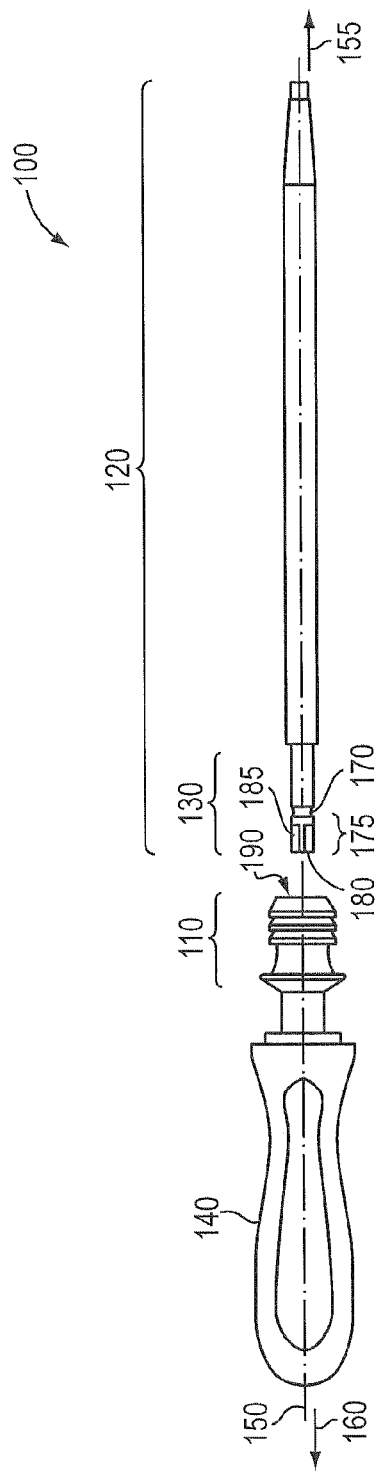
FIG. 1 is a perspective view of an example surgical instrument that includes an example improved quick connect interface (in this example, an improved ¼ inch square quick connect interface) and an example replaceable tool (in this example, a hex bit having a ¼ inch square shaft)
Figure 2:
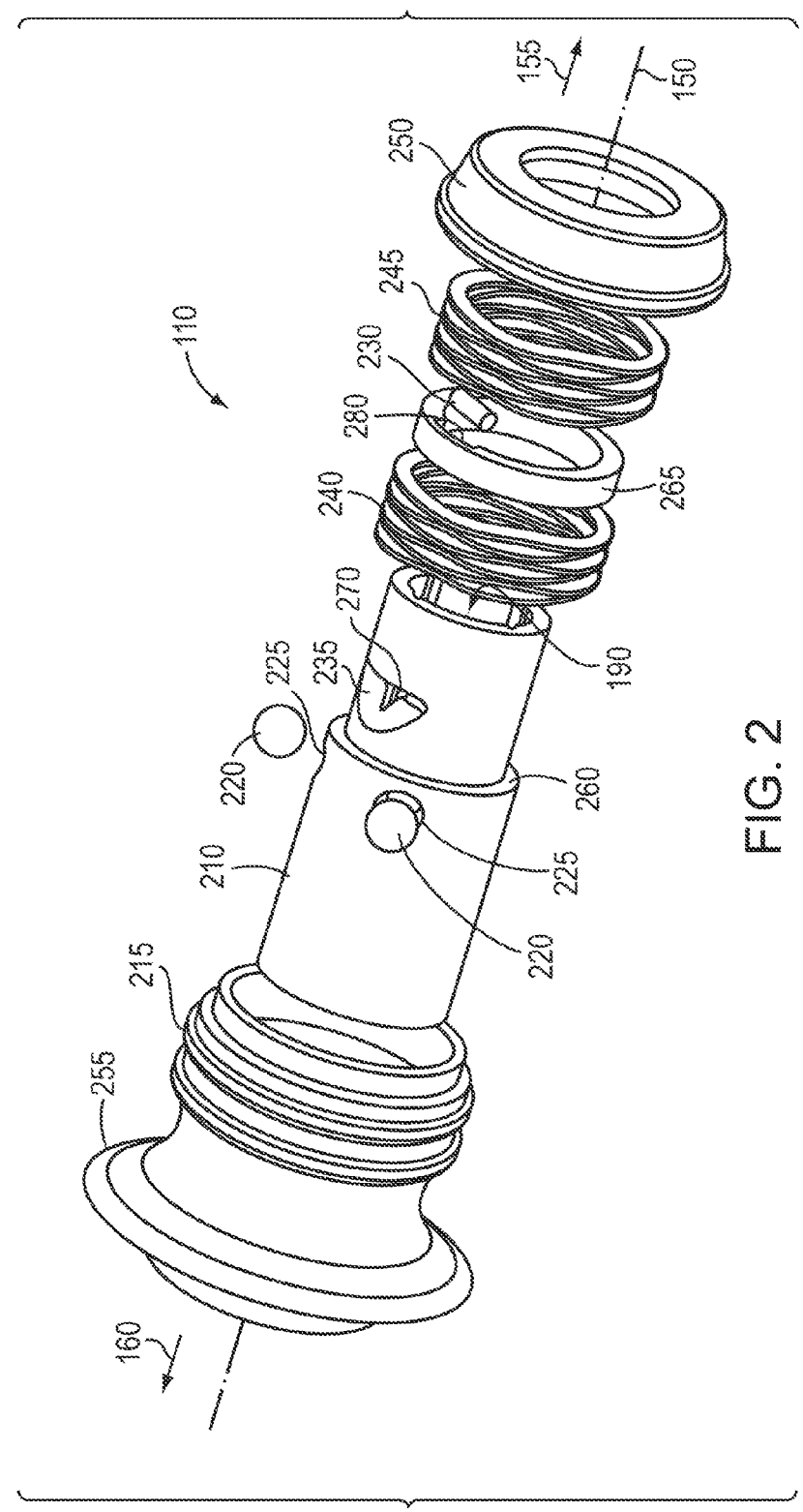
FIG. 2 is an enlarged exploded perspective view of the example improved quick connect interface of FIG. 1, showing its components and their assembly.
Figure 3:
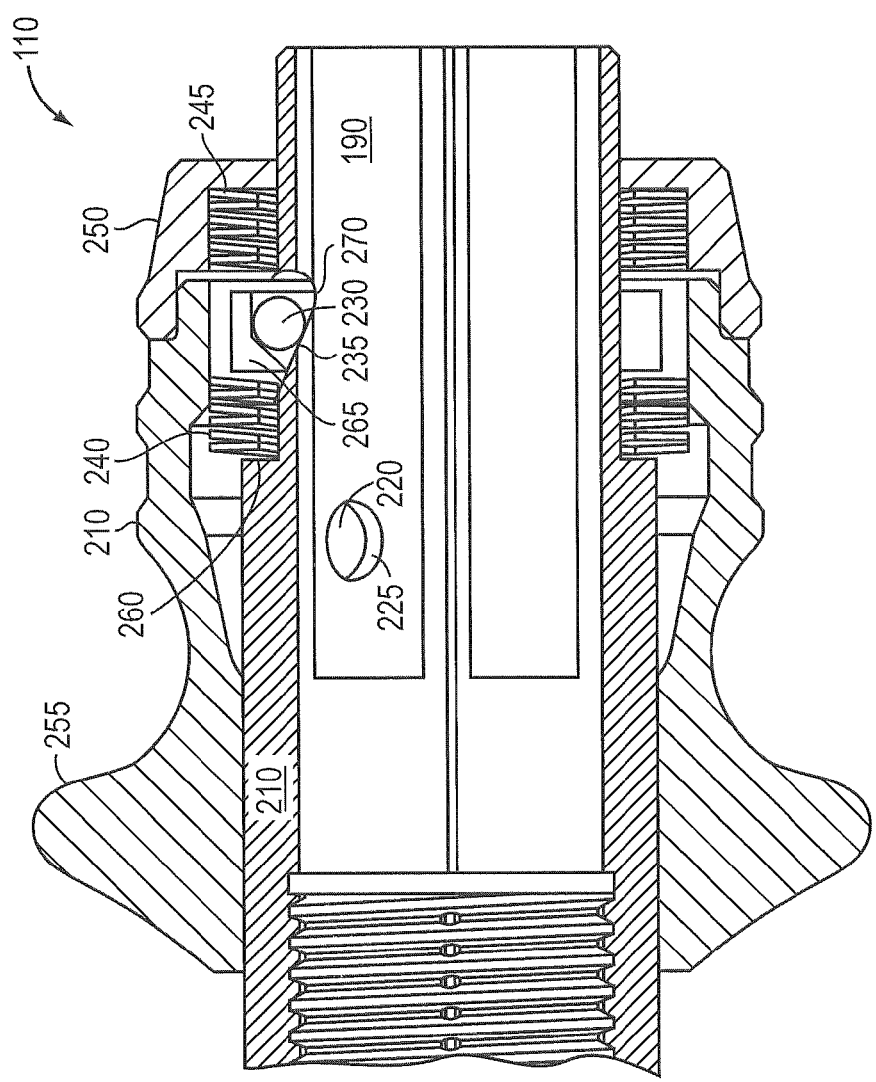
FIG. 3 is an enlarged cut-away side view of the example improved quick connect interface of FIGS. 1 and 2 showing, among other things, ball bearings when the sliding sleeve is in an unlocked position.
Figure 4:
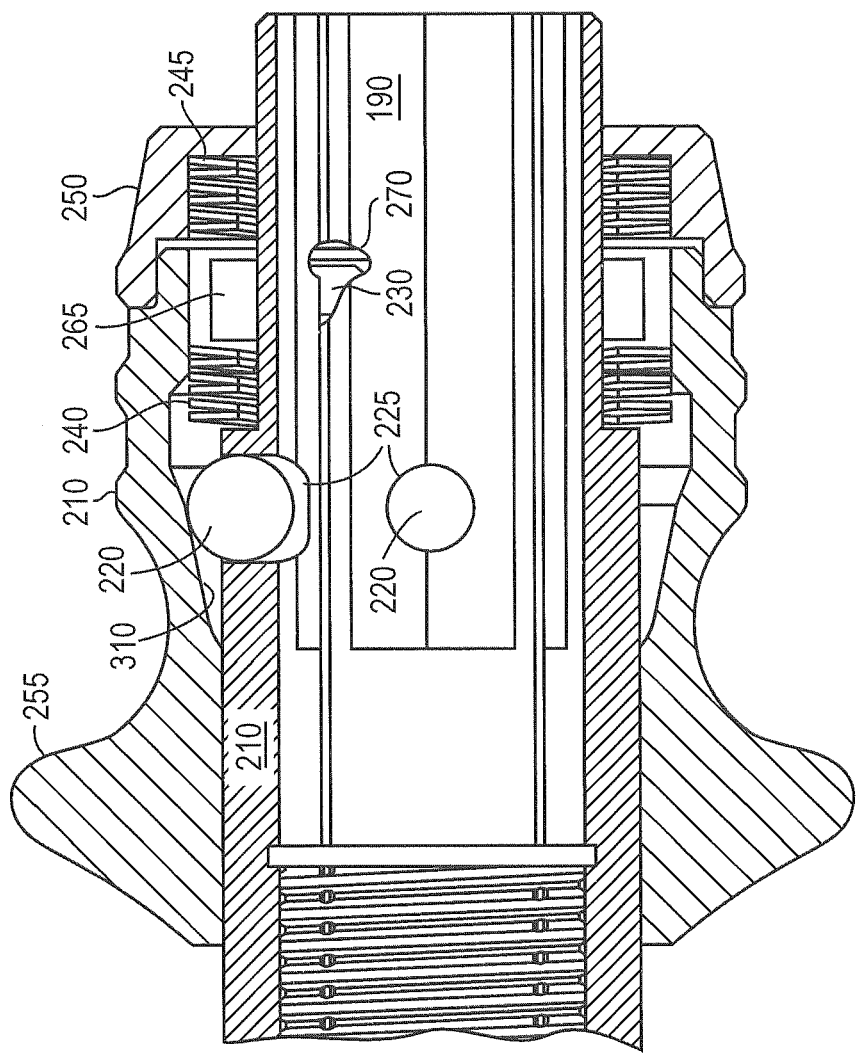
FIG. 4 is an enlarged cut-away top view of the example improved quick connect interface of FIGS. 1-3 showing, among other things, a locking pin when the sliding sleeve is in the unlocked position.

Referring to FIG. 1, an example surgical instrument 100 may include an example improved quick connect interface 110 (in this example, an improved ¼ inch square quick connect interface), and an example replaceable tool 120 (in this example, a hex bit). A drive mechanism 140 is coupled to the improved quick connect interface 110. In this example, the drive mechanism 140 is a non-ratcheting molded handle. Alternatively, other drive mechanisms may be used, including ratcheting and non-ratcheting handles or a motor-operated drive. A central axis 150 may extend through the center of the surgical instrument 100, and in turn the quick connect interface 110. The central axis may extend in both a distal direction 155, and a proximal direction 160.

A shaft 130 (in this example, a ¼ inch square shaft) of the replaceable tool 120 may include a semi-circular groove 170 that extends around the circumference of the shaft 130. The shaft 130 may also include a substantially square portion 175 that has corners 180 and faces 185. The shaft, including the groove 170 and the substantially square portion 175, may be inserted by movement in the proximal direction 160 into an inner cavity 190 of the quick connect interface 110, and secured therein.

Referring to FIGS. 2-7, the example improved quick connect interface 110 includes a generally cylindrical body 210 into which the inner cavity 190 may be formed. The body 210 may have an inner surface that defines the inner cavity, and is shaped to accommodate the shaft 130 of the replaceable tool 120.

A first and a second ball bearing 220 may be positioned in holes 225 in the body 210 that extend from the outer surface to the inner surface. The holes 225 may be sized to permit the ball bearings 220 to extend into the inner cavity 190, but not pass completely therethrough. Each set of holes 225 and ball bearings 220 may be positioned substantially 90 degrees apart from the other, radially about the central axis 150. This positioning may allow the ball bearings 220 to contact the groove 170 near adjacent faces 185 of the shaft 130, when it is inserted into the inner cavity 190.

A generally-cylindrical locking pin 230 may be disposed on a ramp 235 formed in the outer surface of the body 210. The ramp 235 may have an opening 270 at its lower end, which extends from the outer surface to the inner surface of the body 210, and permits the locking pin 230 to extend into the inner cavity 190, but no pass completely therethrough. The locking pin 230 and ramp 235 may be positioned between the first and second ball bearings 220 about the circumference of the body 210, such that the locking pin 230 may contact a corner 180 of the shaft 130 when it is inserted into the inner cavity 190.

A sliding sleeve 215 may surround a portion of the body 210, the first and second ball bearings 220, the locking pin 230 and other components of the quick connect interface 110. The sleeve may be manufactured in multiple portions to permit assembly. For example, it may include a separate cap 250 that is later fitted to the rest of the sleeve 210. The sleeve 215 slides from an unlocked position (FIGS. 3 and 4), where the sleeve is shifted towards a proximal end of the interface 110, to a locked position (FIGS. 5 and 6), where the sleeve 215 is shifted towards a distal end of the interface 110. First and second compression springs (e.g., wave spring) 240, 245 may surround a portion of the body 210, and may urge the sleeve 215 in the distal direction 155, so that, when at rest, the sleeve 215 is in the locked position. The first and second compression springs 240, 245 may be identical to one another. A finger ledge 255 may be formed in the sleeve 215, so that one may pull the sleeve in the proximal direction 160, to the unlocked position, against the resistance of the compression springs 240, 245. The first compression spring 240 may engage a lip 260 formed in the body 210, while the second compression spring 245 may engage the cap 250 of the sleeve 215.

Figure 5:
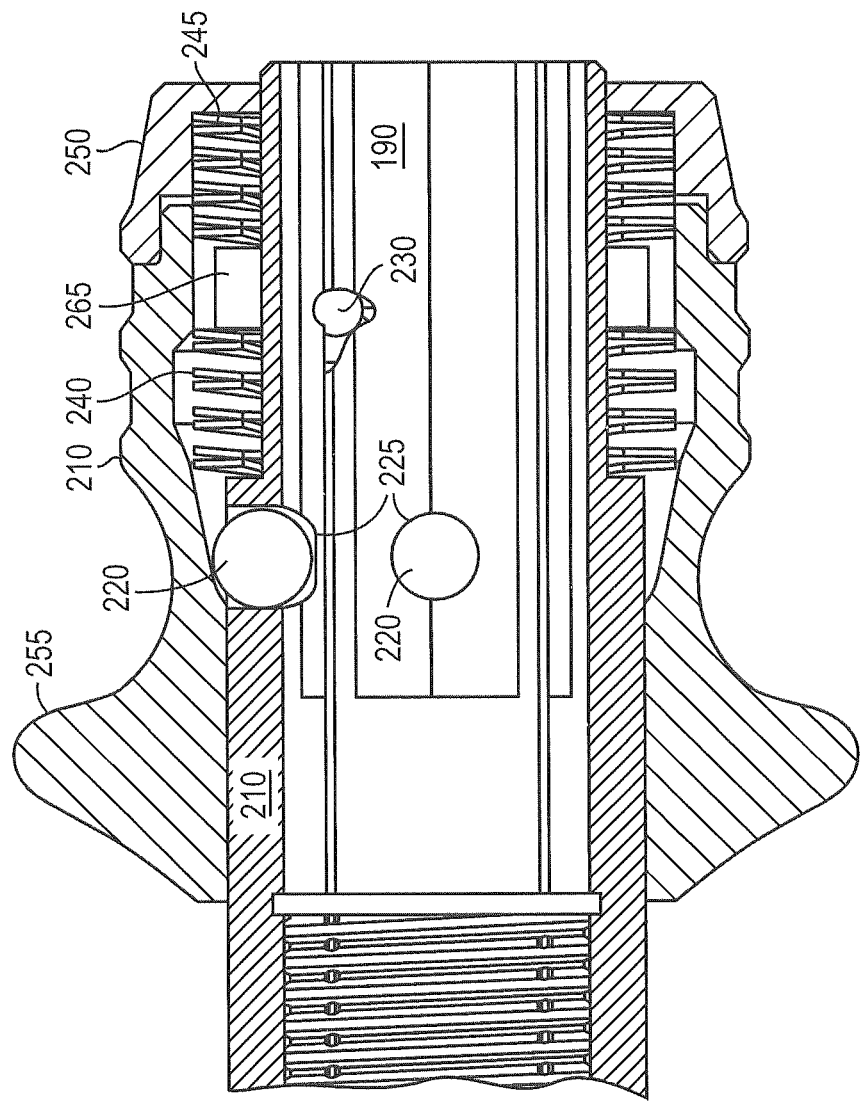
FIG. 5 is an enlarged cut-away side view of the example improved quick connect interface of FIGS. 1-4 showing, among other things, ball bearings when the sliding sleeve is in an locked position.
Figure 6:
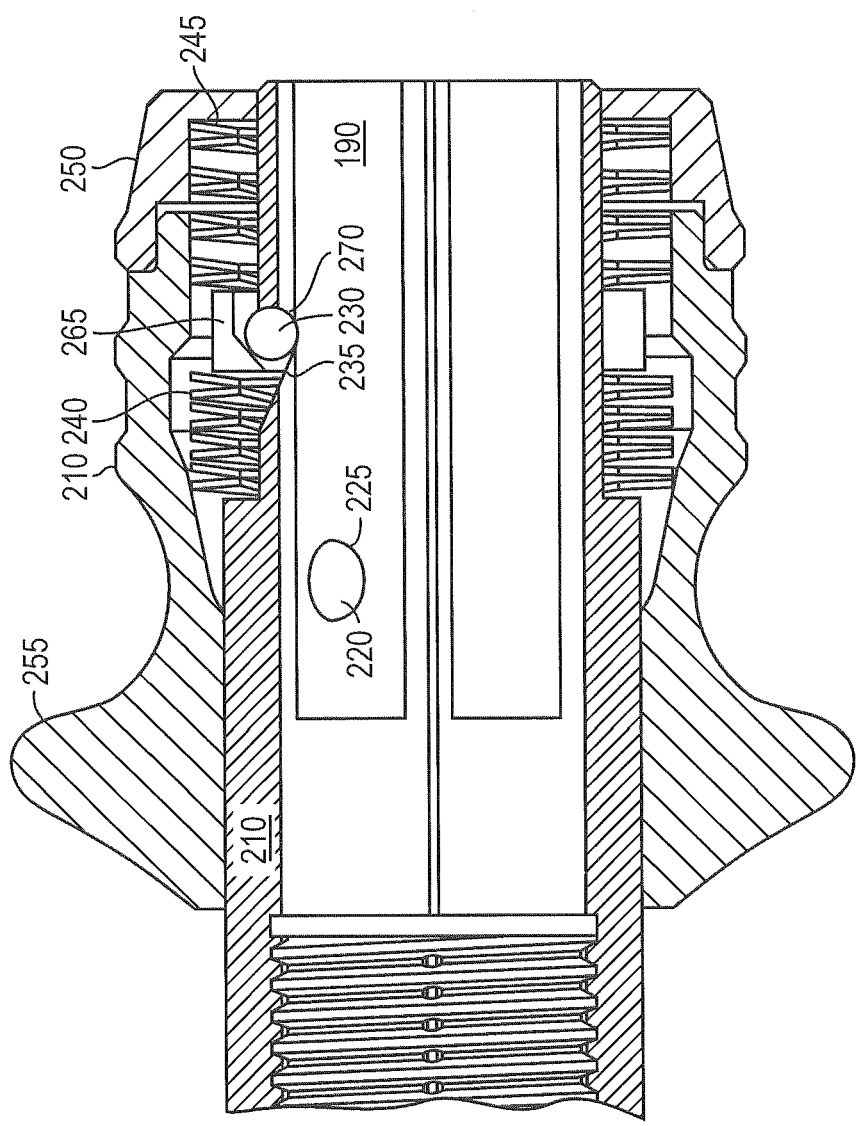
FIG. 6 is an enlarged cut-away top view of the example improved quick connect interface of FIGS. 1-5 showing, among other things, the locking pin when the sliding sleeve is in the locked position.
Figure 7:
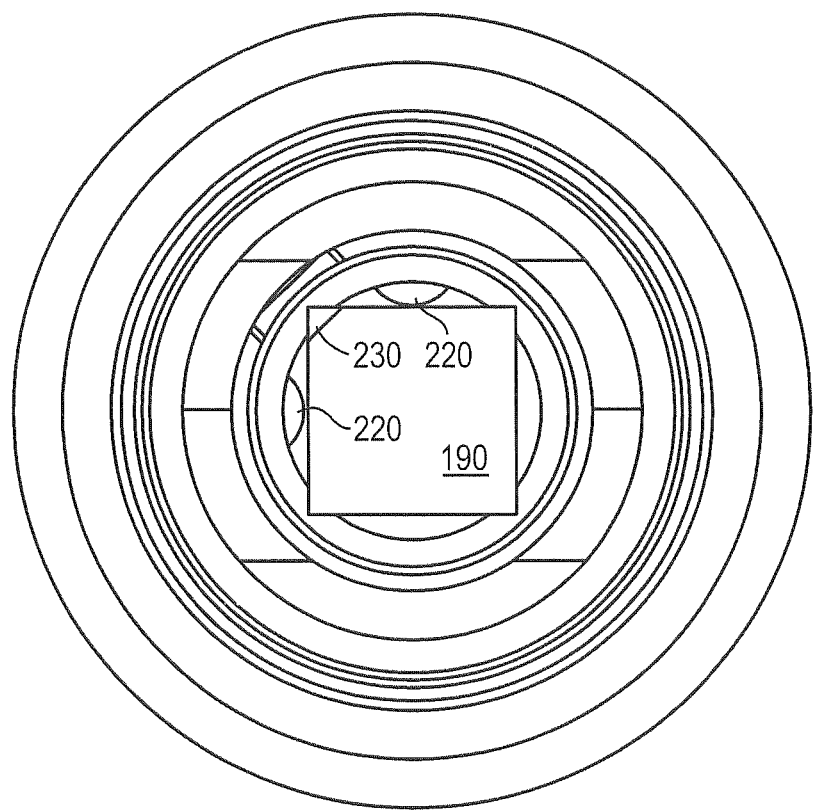
FIG. 7 is an enlarged front view of the example improved quick connect interface of FIGS. 1-6 showing, among other things, the positioning of the ball bearings and locking pin to urge the shaft of the replaceable tool towards one side of the inner cavity.

Referring to FIGS. 3-6, a camming ramp 310 may be formed in an interior surface of the sleeve, proximate the ball bearings 220. As the sleeve 215 is slide from the unlocked position (FIGS. 3 and 4) to the locked position (FIGS. 5 and 6), the ball bearings 220 may be urged by contact with the camming ramp 310 into the holes 225, so that they partially extend through the holes 225 into the inner cavity 190. When so urged, they may engage the groove 170 formed in the shaft 170 of a replaceable tool 120 disposed therein. The camming ramp 310, in conjunction with the compression springs 240, 245, may cause the ball bearings to apply pressure to the groove 170 when the sliding sleeve is in the locked position (FIGS. 5 and 6). Since the ball bearings are positioned substantially 90 degrees apart radially about the central axis 150, much of this pressure is incident upon one side of the shaft 130 of the replaceable tool 120. The shaft 130 is thereby urged towards one side (e.g., corner) of the inner cavity 190 of the body 210.

The locking pin 230 may be guided by a slideable shuttle 265 that forms a ring surrounding a portion of the body 210, and that is enclosed by the sliding sleeve 215. Straight side faces of a cutout 280 in the shuttle 265 may aid in retaining the locking pin 230. At least a portion of a top face of the cut out 280 may be angled to assist in directing the locking pin down the ramp 235. The shuttle 265 may be disposed between the first compression spring 240 and the second compression spring 245. The first and second compression spring 240, 245 may be arranged such that, when the sleeve 215 is in the locked position (FIGS. 5 and 6), the first compression spring 240 has a higher preload than the second compression spring 245. The first compression spring 240 thereby applies pressure upon the shuttle 265, which in turn urges the locking pin 230 down the ramp 235, so that it partially extends through the opening 270 at the bottom of the ramp 235, into the inner cavity 190.

Since the locking pin 230 is positioned between the ball bearings 220, the locking pin may apply pressure to a corner 180 of the shaft between where the ball bearings 220 apply their pressure. The additional pressure applied by the locking pin 230 is thereby incident upon the same side of the shaft 130, to further urge it urged towards one side (e.g., corner) of the inner cavity 190 of the body 210. This urging may ensure firm contact despite variations in the shafts of replaceable tools, and thereby reduce both lateral and axial play.

When the sleeve 215 is returned to the unlocked position (FIGS. 3 and 4), pressure on the ball bearings 220 from the camming ramp 310 may be removed, and the preload on the first compression spring 240 and the second compression spring 250 may be adjusted into equilibrium. The ball bearings 220 are allowed to recess in their holes 225 from the inner cavity 190, and the locking pin 230 may travel up the ramp 235 away from the opening 270, to likewise recess from the inner cavity 190. The shaft 130 of the replaceable tool 120 may then be removed from the quick connect interface 110.

While the above description discusses at least one embodiment of the improved quick connect interface, it should be apparent that a number of other embodiments may be implemented. Such embodiments may include a wide variety of modification and/or additions to what is described above, to embrace this disclosure's intended spirit and scope.

For example, in one alternative embodiment, the camming ramp 310 may be formed with a special plateau feature that acts to prevent unintentional release of the shaft 130 of the replaceable tool 120. Unintentional release could occur if sufficient force were exerted upon the replaceable tool 120 in the distal direction 155. This force would be transmitted by the shaft 130, to the ball bearings 220, which in turn would transmit it to the camming ramp 310 and the sleeve 215. If the force upon the sleeve 215 exceeds the force exerted by the compression springs 240, 245 that maintain the sleeve in the locked position, the sleeve will retract, and the shaft 130 will be unintentionally released.

Figure 8:
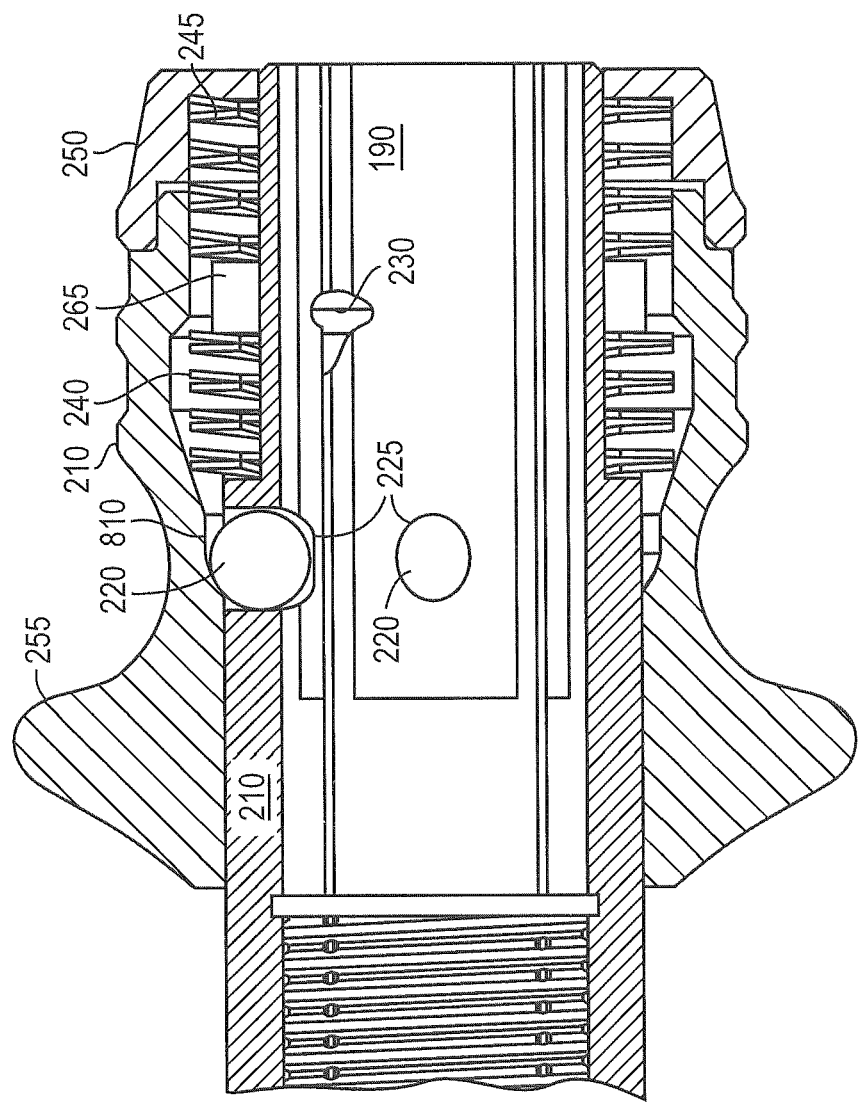
FIG. 8 is an enlarged cut-away side view of an alternative embodiment of the improved quick connect showing, among other things, a plateau in the camming ramp that operates to interrupt unintentional removal.

Referring to FIG. 8, a plateau 810 may be disposed in the camming ramp 310, proximate the bottom of the ramp, near location of the ball bearings 220 when the sleeve 215 is in the locked position. The plateau 810 may be a substantially flat region that is oriented substantially parallel to the central axis 150, in contrast to the generally angled profile of the camming ramp 310. Should force be exerted in a distal direction 155 upon the replaceable tool 130, and the ball bearings 220 begin to move up the camming ramp 310, their travel will be interrupted by the plateau 810. When they encounter the plateau 810, due to the lack of angle, the ball bearings 220 will no longer be able to exert force onto the camming ramp 310 in a direction parallel to the central axis 150, and thereby will not cause the sleeve 215 to retract. In this manner, unintentional release is prevented.

Further, while it is discussed above that the quick connect interface may be a ¼ inch square quick connect interface, it should be understood that at least some of the techniques may be applied to other types of interface, for example, to AO pull, AO push, Zimmer, Hudson or other types of interfaces.

Similarly, while it is discussed above that two ball bearings and a single locking pin are used, it should be understood that a different number of ball bearings and locking pins may be used in other embodiments. For example, a single ball bearing may be employed, or two locking pins may be used.

Further, while it is discussed above that first and second compression springs (e.g., wave springs) may, by virtue of differing preload, act upon a shuttle, it should be understood that other means may be used for urging the locking pin down the ramp. For example, in some arrangements, a dedicated compression spring may be employed that acts upon the shuttle or directly upon the locking pin, or one or more tension springs may be employed that act upon the shuttle or some other structure.

Further, while certain approximate angles are discussed above, a variety of other angles may alternatively be employed, depending on the particular implementation. As used herein, when an angle is stated to be "substantially" of a certain degree measure, it should be understood that measures of up to plus or minus 10 degrees of the stated angle are to be considered substantially of that degree measure.

Further, it should be understood that a quick connect interface may be constructed from a variety of materials, including stainless steel, aluminum, other metals, plastics, and combinations thereof.

In general, it should be understood that the above descriptions are meant to be taken only by way of example.

What is claimed is:

1. A quick connect interface for a surgical instrument, comprising:
    a body having an outer surface, and having an inner surface which defines an inner cavity that is shaped to accommodate a shaft of a replaceable tool;
    one or more ball bearings that are each disposed in a respective hole in the body that extends from the outer surface to the inner surface of the body;
    a substantially cylindrical locking pin that is disposed on a ramp formed in the outer surface of the body, the ramp having an opening that extends from the outer surface to the inner surface of the body;
    a sleeve that surrounds a portion of the body and is slideable along the body, from an unlocked position to a locked position, the sleeve including a camming ramp that contacts the one or more ball bearings, the camming ramp arranged to urge the one or more ball bearings to partially extend through the holes into the inner cavity when the sleeve is in the locked position;
    one or more springs arranged to urge the substantially cylindrical locking pin down the ramp formed in the outer surface of the body, so that a side of the substantially cylindrical locking pin partially extends through the opening into the inner cavity when the sleeve is in the locked position,
    wherein the one or more ball bearings and the substantially cylindrical locking pin are positioned such that, when the shaft of the replaceable tool is disposed in the inner cavity, the one or more ball bearings and the side of the substantially cylindrical locking pin will contact the shaft and urge the shaft to one side of the inner cavity.

2. The quick connect interface of claim 1, wherein the one or more springs include a first compression spring and a second compression spring that act upon the substantially cylindrical locking pin, the first compression spring having a higher preload than the second compression spring when the sleeve is in the locked position, the higher preload to urge the substantially cylindrical locking pin down the ramp.

3. The quick connect interface of claim 2, further comprising;
    a slideable shuttle disposed between the first compression spring and the second compression spring, the shuttle having a cutout in which the substantially cylindrical locking pin is retained, the higher preload when the sleeve is in the locked position to apply pressure upon the shuttle which in turn urges the substantially cylindrical locking pin down the ramp.

4. The quick connect interface of claim 3, wherein the slideable shuttle forms a ring surrounding a portion of the body.

5. The quick connect interface of claim 2, wherein the first compression spring and the second compression spring are identical springs.

6. The quick connect interface of claim 2, wherein the first compression spring and the second compression are wave springs that surround a portion of the body and are enclosed by the sleeve.

7. The quick connect interface of claim 1, wherein the one or more ball bearings are first and second ball bearings positioned radially about a central axis of the body substantially 90 degrees apart, wherein there are no additional ball bearings positioned radially about the central axis opposing the first and second ball bearings.

8. The quick connect interface of claim 7, wherein the substantially cylindrical locking pin is positioned radially about the central axis between the first and second ball bearings so that the side of the substantially cylindrical locking pin partially extends into the inner cavity between the first and second ball bearings to contact the shaft of the replaceable tool when disposed in the inner cavity, wherein there is no additional locking pin positioned radially about the central axis opposing the substantially cylindrical locking pin.

9. The quick connect interface of claim 1, wherein the camming ramp includes a plateau that prevents unintentional release of the shaft of the replaceable tool.

10. The quick connect interface of claim 1, wherein the quick connect interface is a ¼ inch square quick connect interface, the inner cavity is shaped to accommodate a ¼ inch square shaft, the one or more ball bearings are positioned to engage a semi-circular groove of the ¼ inch square shaft, and the substantially cylindrical locking pin is positioned to engage a corner of a substantially square portion of the ¼ inch square shaft.

11. A surgical instrument that includes a quick connect interface, comprising:
   a drive mechanism;
   a replaceable tool having a shaft; and
   a quick connect interface coupled to the drive mechanism, and configured to connect to the shaft of the replaceable tool, the quick connect interface including:
      a body having an outer surface, and having an inner surface which defines an inner cavity that is shaped to accommodate the shaft of the replaceable tool,
      one or more ball bearings that are each disposed in a respective hole in the body,
      a substantially cylindrical locking pin that is disposed on a ramp formed in the body, the ramp having an opening,
      a sleeve that surrounds a portion of the body and is slideable along the body, from an unlocked position to a locked position, the sleeve including a camming ramp that contacts the one or more ball bearings, the camming ramp arranged to urge the one or more ball bearings to partially extend through the holes into the inner cavity when the sleeve is in the locked position,
      one or more springs arranged to urge the substantially cylindrical locking pin down the ramp, so that a side of the substantially cylindrical locking pin partially extends through the opening into the inner cavity when the sleeve is in the locked position,
      wherein the one or more ball bearings and the substantially cylindrical locking pin are positioned such that, when the shaft of the replaceable tool is disposed in the inner cavity, the one or more ball bearings and the side of the substantially cylindrical locking pin will contact the shaft and urge the shaft to one side of the inner cavity.

12. The surgical instrument of claim 11, wherein the one or more springs include a first compression spring and a second compression spring that act upon the locking pin, the first compression spring having a higher preload than the second compression spring when the sleeve is in the locked position, the higher preload to urge the substantially cylindrical locking pin down the ramp.

13. The surgical instrument of claim 12, further comprising:
   a slideable shuttle disposed between the first compression spring and the second compression spring, the shuttle having a cutout in which the locking pin is retained, the higher preload when the sleeve is in the locked position to apply pressure upon the shuttle which in turn urges the locking pin down the ramp.

14. The surgical instrument of claim 12, wherein the first compression spring and the second compression spring are identical wave springs that surround a portion of the body and are enclosed by the sleeve.

15. The surgical instrument of claim 11, wherein the one or more ball bearings are first and second ball bearings positioned radially about a central axis of the body substantially 90 degrees apart, wherein there are no additional ball bearings positioned radially about the central axis opposing the first and second ball bearings.

16. The surgical instrument of claim 15, wherein the substantially cylindrical locking pin is positioned radially about the central axis between the first and second ball bearings so that the side of the substantially cylindrical locking pin partially extends into the inner cavity between the first and second ball bearings to contact the shaft of the replaceable tool when disposed in the inner cavity, wherein there is no additional locking pin positioned radially about the central axis opposing the locking pin.

17. The surgical instrument of claim 15, wherein the camming ramp includes a plateau that prevents unintentional release of the shaft of the replaceable tool.

18. The surgical instrument of claim 15, wherein the quick connect interface is a ¼ inch square quick connect interface, and the shaft of the replaceable tool is a ¼ inch square shaft.

19. A quick connect interface for a surgical instrument, comprising:
   an inner cavity sized to accommodate a shaft of a replaceable tool;
   one or more ball bearings that are each disposed in a respective hole;
   a substantially cylindrical locking pin that is disposed on a ramp, the ramp having an opening;
   a sleeve that is slideable from an unlocked position to a locked position, the sleeve including a camming ramp that contacts the one or more ball bearings, the camming ramp arranged to urge the one or more ball bearings to partially extend through the holes into the inner cavity when the sleeve is in the locked position;
   means for urging the substantially cylindrical locking pin down the ramp so that a side of the cylindrical locking pin partially extends through the opening into the inner cavity when the sleeve is in the locked position,
   wherein the one or more ball bearings and the substantially cylindrical locking pin are positioned such that, when the shaft of the replaceable tool is disposed in the inner cavity, the one or more ball bearings and the side of the substantially cylindrical locking pin will contact the shaft and urge the shaft to one side of the inner cavity.

20. The quick connect interface of claim 19, wherein the one or more ball bearings are first and second ball bearings positioned radially about a central axis of the body substantially 90 degrees apart, wherein there are no additional ball bearings positioned radially about the central axis opposing the first and second ball bearings.

21. A quick connect interface for a surgical instrument, comprising:
   a body having an inner surface which defines an inner cavity that is shaped to accommodate a shaft of a replaceable tool;
   first and second ball bearings that are positioned radially about a central axis of the body substantially 90 degrees apart, the first and second ball bearings each disposed in a respective hole in the inner surface of the body;
   a substantially cylindrical locking pin that is positioned radially about the central axis between the first and second ball bearings, the substantially cylindrical locking pin disposed in an opening in the inner surface of the body;
   a sleeve that surrounds a portion of the body and is slideable along the body, from an unlocked position to a locked position, the sleeve to urge the one or more ball bearings to partially extend through the holes into the inner cavity when the sleeve is in the locked position, wherein there are no additional ball bearings or locking pins positioned radially about the central axis opposing the first and second ball bearings and the substantially cylindrical locking pin, such that, when the shaft of the replaceable tool is disposed in the inner cavity, the first and second ball bearings and a side of the substantially cylindrical locking pin will contact the shaft and urge the shaft to one side of the inner cavity.

22. The quick connect interface of claim 21, wherein the substantially cylindrical locking pin is disposed on a ramp and the quick connect interface further comprises:

one or more springs arranged to urge the substantially cylindrical locking pin down the ramp to urge the substantially cylindrical locking pin to partially extend through the opening into the inner cavity when the sleeve is in the locked position.

23. The quick connect interface of claim 21, wherein the quick connect interface is a ¼ inch square quick connect interface, the substantially cylindrical locking pin is so positioned such that when a ¼ inch square shaft is disposed in the inner cavity the substantially cylindrical locking pin will engage a corner of the ¼ inch square shaft, and the one side of the inner cavity is a corner of the inner cavity.

24. A surgical instrument that includes a quick connect interface, comprising:

a drive mechanism;

a replaceable tool having a shaft; and a quick connect interface coupled to the drive mechanism, and configured to connect to the shaft of the replaceable tool, the quick connect interface including:

a body having an inner surface which defines an inner cavity that is shaped to accommodate a shaft of a replaceable tool, first and second ball bearings that are positioned radially about a central axis of the body substantially 90 degrees apart, the first and second ball bearings each disposed in a respective hole in the inner surface of the body, a substantially cylindrical locking pin that is positioned radially about the central axis between the first and second ball bearings, the substantially cylindrical locking pin disposed in an opening in the inner surface of the body, and a sleeve that surrounds a portion of the body and is slideable along the body, from an unlocked position to a locked position, the sleeve to urge the one or more ball bearings to partially extend through the holes into the inner cavity when the sleeve is in the locked position, wherein there are no additional ball bearings or locking pins positioned radially about the central axis opposing the first and second ball bearings and the substantially cylindrical locking pin, such that, when the shaft of the replaceable tool is disposed in the inner cavity, the first and second ball bearings and a side of the substantially cylindrical locking pin will contact the shaft and urge the shaft to one side of the inner cavity.

25. The surgical instrument of claim 24, wherein the substantially cylindrical locking pin is disposed on a ramp and the quick connect interface further includes:

one or more springs arranged to urge the substantially cylindrical locking pin down the ramp to partially extend through the opening into the inner cavity when the sleeve is in the locked position.

26. The surgical instrument of claim 24, wherein the quick connect interface is a ¼ inch square quick connect interface, the shaft of the replaceable tool is a ¼ inch square shaft, and the substantially cylindrical locking pin is positioned to engage a corner of the ¼ inch square shaft, and the one side of the inner cavity is a corner of the inner cavity.

* * * * *